US007920676B2

(12) United States Patent
Yun et al.

(10) Patent No.: US 7,920,676 B2
(45) Date of Patent: Apr. 5, 2011

(54) CD-GISAXS SYSTEM AND METHOD

(75) Inventors: Wenbing Yun, Walnut Creek, CA (US);
Yuxin Wang, Northbrook, IL (US);
Srivatsan Seshadri, Walnut Creek, CA (US); Kenneth W. Nill, Lexington, MA (US)

(73) Assignee: Xradia, Inc., Pleasanton, CA (US)

( * ) Notice: Subject to any disclaimer, the term of this patent is extended or adjusted under 35 U.S.C. 154(b) by 161 days.

(21) Appl. No.: 11/774,183

(22) Filed: Jul. 6, 2007

(65) Prior Publication Data
US 2008/0273662 A1    Nov. 6, 2008

Related U.S. Application Data

(60) Provisional application No. 60/916,122, filed on May 4, 2007, provisional application No. 60/941,170, filed on May 31, 2007.

(51) Int. Cl.
*G01N 23/20* (2006.01)
(52) U.S. Cl. ................................ 378/86; 378/70; 378/71
(58) Field of Classification Search .................... 378/70, 378/71, 84, 85, 89
See application file for complete search history.

(56) References Cited

U.S. PATENT DOCUMENTS

| | | | | | |
|---|---|---|---|---|---|
| 2,831,977 | A | * | 4/1958 | Henke | 378/70 |
| 4,951,304 | A | * | 8/1990 | Piestrup et al. | 378/84 |
| 5,588,034 | A | * | 12/1996 | Bowen et al. | 378/70 |
| 5,619,548 | A | | 4/1997 | Koppel | |
| 5,740,226 | A | * | 4/1998 | Komiya et al. | 378/70 |
| 5,784,432 | A | * | 7/1998 | Kurtz et al. | 378/70 |
| 5,923,720 | A | * | 7/1999 | Barton et al. | 378/84 |
| 6,160,867 | A | * | 12/2000 | Murakami | 378/84 |
| 6,389,101 | B1 | * | 5/2002 | Levine et al. | 378/85 |
| 6,453,002 | B1 | * | 9/2002 | Mazor et al. | 378/82 |
| 6,483,892 | B1 | * | 11/2002 | Wang et al. | 378/43 |
| 6,507,636 | B1 | * | 1/2003 | Lehmann | 378/73 |
| 6,556,652 | B1 | | 4/2003 | Mazor et al. | |
| 6,633,831 | B2 | | 10/2003 | Nikoonahad et al. | |
| 6,697,454 | B1 | * | 2/2004 | Nicolich et al. | 378/85 |
| 6,710,341 | B2 | * | 3/2004 | Terauchi | 378/90 |
| 6,771,735 | B2 | * | 8/2004 | Janik et al. | 378/70 |
| 6,895,075 | B2 | | 5/2005 | Yokhin et al. | |

(Continued)

FOREIGN PATENT DOCUMENTS

WO    02/13232 A2    2/2002

(Continued)

OTHER PUBLICATIONS

Jones et al., "Small angle x-ray scattering for sub-100 nm pattern characterization", Applied Physics Letters, vol. 83, No. 19, (Nov. 10, 2003), pp. 4059-4061.*

(Continued)

*Primary Examiner* — Chih-Cheng G Kao
(74) *Attorney, Agent, or Firm* — Houston Eliseeva, LLP

(57) ABSTRACT

CD-GISAXS achieves reduced measurement times by increasing throughput using longer wavelength radiation (~12×, for example) such as x-rays in reflective geometry to increase both the collimation acceptance angle of the incident beams and the scattering signal strength, resulting in a substantial combined throughput gain. This wavelength selection and geometry can result in a dramatic reduction in measurement time. Furthermore, the capabilities of the CD-GISAXS can be extended to meet many of the metrology needs of future generations of semiconductor manufacturing and nanostructure characterization, for example.

71 Claims, 6 Drawing Sheets

U.S. PATENT DOCUMENTS

| | | | |
|---|---|---|---|
| 6,925,147 B2 * | 8/2005 | Lange et al. ............... | 378/84 |
| 6,972,852 B2 | 12/2005 | Opsal et al. | |
| 7,003,075 B2 * | 2/2006 | Miyake et al. ............. | 378/70 |
| 7,068,753 B2 | 6/2006 | Berman et al. | |
| 7,072,442 B1 * | 7/2006 | Janik ......................... | 378/84 |
| 7,110,491 B2 | 9/2006 | Mazor et al. | |
| 7,113,566 B1 * | 9/2006 | Peled et al. ................ | 378/70 |
| 7,120,228 B2 | 10/2006 | Yokhin et al. | |
| 7,158,609 B2 * | 1/2007 | Kikuchi et al. ............. | 378/70 |
| 7,295,650 B2 * | 11/2007 | Lange et al. ............... | 378/70 |
| 2001/0028699 A1 * | 10/2001 | Iwasaki ...................... | 378/84 |
| 2002/0080916 A1 * | 6/2002 | Jiang et al. ................. | 378/84 |
| 2003/0156682 A1 * | 8/2003 | Yokhin et al. ............. | 378/70 |
| 2004/0156474 A1 * | 8/2004 | Yokhin et al. ............. | 378/70 |
| 2005/0105684 A1 * | 5/2005 | Bruegemann et al. ..... | 378/71 |
| 2005/0259790 A1 * | 11/2005 | Gerndt et al. .......... | 378/98.12 |
| 2006/0083350 A1 * | 4/2006 | Gerndt et al. ............. | 378/70 |
| 2006/0133569 A1 * | 6/2006 | Michaelsen et al. ....... | 378/70 |
| 2006/0133570 A1 | 6/2006 | Mazor et al. | |
| 2006/0274886 A1 | 12/2006 | Mazor et al. | |
| 2007/0201615 A1 * | 8/2007 | Zienert et al. ............. | 378/73 |

FOREIGN PATENT DOCUMENTS

WO          02/13232 A3    2/2002

OTHER PUBLICATIONS

Hu et al., "Small angle x-ray scattering metrology for sidewall angle and cross section of nanometer scale line gratings", Journal of Applied Physics, vol. 96, No. 4, (Aug. 15, 2004), pp. 1983-1987.*

Goldstein, J. I., et al., Scanning Electron Microscopy and X-Ray Microanalysis, Plenum Press, New York, Chapter 3, 1992, nb pp. 76-78, 118-130, and 127-129.

Gstir, B., et al., "Calculated cross sections for the K-shell ionization of chromium, nickel, copper, scandium and vanadium using the DM formalism," Jour. Phys. B: At. Mol. Opt. Phys., 34, 3372-3382, 2001.

Bunday, B. et al., "Major Trends in Extending CD-SEM Utility," Proc. SPIE Int. Soc. Opt. Eng. 6518, 651835 (2007).

Bunday, B. et al., "Realizing 'Value-Added' Metrology," Proc. SPIE Int. Soc. Opt. Eng. 6518, 65181K (2007).

Bunday, B. et al., "SEM Metrology for Advanced Lithographies," Proc. SPIE Int. Soc. Opt. Eng. 6518, 65182B (2007).

Diebold, A. C., "Metrology Technology for the 70-nm Node: Process Control Through Amplification and Averaging Microscopic Changes," IEEE Transactions on Semiconductor Manufacturing, 15, 169-182, 2002.

Lazzari, R., "IsGISAXS: a program for grazing-incidence small-angle X-ray scattering analysis of supported islands," J. Appl. Cryst., 35, 406-421, 2002.

Jones, R.L. et al., "Critical Dimension Metrology of Nanoscale Structures with Small Angle X-ray Scattering," Proc. SPIE 5038, 191 (2003).

U.S. Appl. No. 11/609,266, by Wenbing Yun, filed Dec. 11, 2006.

Lee, H. J. et al., "Characterizing Patterned Structures Using X-ray Reflectivity," SPIE, 6518, 651813 (2007).

Wang, C. et al., "Line Width Roughness Characterization of Sub-50nm Structures using CD-SAXS," SPIE, 6518, 651810 (2007).

"International Technology Roadmap for Semiconductors: Metrology," 2006 Update.

"International Technology Roadmap for Semiconductors: Overview and Working Group Summaries," 2006 Update.

"Critical Dimension and Overlay Metrology Program," "Semiconductor Microelectronics and Nanoelectronics Programs at NIST," Jul. 2007.

Duparre, A. et al., "Surface Characterization of Optical components for the DUV, VUV and EUV," Microelectronic Engineering 57-58, 65-70 (2001).

Bunday, B. et al., "The Coming of Age of Tilt CD-SEM," SPIE, 6518, 65181S (2007).

Braun, A. E., "Sidewall Metrology Expects Clear Sailing to 32 nm," Semiconductor International (Mar. 1, 2007).

Elliott, R. et al., "CD SEM Measurement of Dual Inlaid Copper Interconnect," Yield Management Solutions, C-26-27 (Autumn 1999).

* cited by examiner

CD-GISAXS SYSTEM AND METHOD

RELATED APPLICATIONS

This application claims the benefit under 35 USC 119(e) of U.S. Provisional Application Nos. 60/916,122, filed on May 4, 2007, and 60/941,170, filed on May 31, 2007, both of which are incorporated herein by this reference in their entirety.

BACKGROUND OF THE INVENTION

A critical dimension (CD) of a semiconductor device refers to a feature that has a direct impact on the device's performance or its manufacturing yield. Therefore, CD's must be manufactured or controlled to tight specifications. Examples of CD's include gate length, gate width, interconnect line width, line spacing, and line width roughness (LWR), to list a few examples. Semiconductor devices are very sensitive to these dimensions and even minute variations can lead to large degradations in their performance, device failure, or manufacturing yield.

As integrated circuit (IC) feature sizes of semiconductor devices continue to shrink, manufacturers face ever decreasing process windows and tighter tolerances. This has dramatically raised the accuracy and sensitivity requirements for CD metrology tools as well as the need for non-destructive measurement sampling early in the manufacturing cycle with minimal impact to productivity of the semiconductor device manufacturing plant or fab. Furthermore, because of the high-aspect ratio features used in IC's today, the need for three dimensional (3D) profile information on device structures, including sidewall angle, and top and bottom dimensions, has become critical. An exemplary driver of this need is the 3d gate structures used in new transistor designs. Consequently, the ability to measure the 3D profile provides far more valuable information than the conventional two dimensional line width and spacing CD information.

Historically, CD measurements were made with optical microscopes, but as dimensions shrank to sub-micron scales, electron microscopes (CD-SEM) became an alternative solution in recent years. Another solution is an optical technique developed by International Business Machines Corporation, Inc. (IBM) and later commercialized by Nanometrics Incorporated using scatterometry to make CD measurements with visible light. Taking advantage of low-cost computing power, this method measures the diffraction patterns from a sample illuminated with visible light and determines the CD parameter using a combination of look-up data library and an inverse computing model based on the rigorous coupled wave analysis (RCWA). Often referred to as optical critical dimension (OCD) metrology, it is a non-destructive and high-throughput technique that has been widely used for process control. Other techniques such as atomic force microscopy (AFM) have also been applied to CD measurement, but wide use of AFM, for example, has been limited by its measurement speed and probe size.

As IC feature dimensions approach 32 nanometers (nm), the metrology requirements push these technologies to their fundamental limits. The disadvantages of CD-SEM have become more critical: 1) the well known charging problem limits the achievable resolution for IC metrology applications; 2) radiation damage induced dimensional shrinking of resists (note: this is particularly problematic with some 193 nm photoresists, for example, that shrink when exposed to electron beams, leading to "CD slimming"); 3) incompatibility with some low-k dielectrics; and 4) CD-SEM is essentially a surface technique making it difficult to measure 3D profiles. Similarly, OCD faces a number of fundamental difficulties: (1) its long wavelength is significantly larger than the device feature size and therefore does not provide a simple and direct measurement; 2) it requires extensive modeling and interpolation, thus compromising the measurement sensitivity. Moreover, over the last decades, use of shorter and shorter wavelengths has been necessitated by the reduction of circuit feature size. Currently the most advanced OCD system uses the deep ultraviolet (DUV) and further incremental reduction in wavelength is not practical because of the extremely low transmission of shorter wavelength radiation in solids or even in low vacuum. This results in numerous problems, including low probing depth, lack of suitable optics, and stringent vacuum requirements. These fundamental limitations have made it practically impossible to extend these existing technologies to meet the critical dimensional control requirements of next generation IC fabrication.

Recognizing the limitations of the existing CD metrology tools, CD metrology and 3D structure characterization have been identified as a Grand Challenge in the International Roadmap for Semiconductors (ITRS) published by SEMATECH. Nearly all existing CD metrology technologies show significant difficulties for node sizes approaching 45 nm and significant research effort is expected to determine a viable solution for future generation ICs.

Dr. Wenli Wu, et. al. at the National Institute of Standards and Technology (NIST) has recently pioneered a new solution for future CD metrology based on a small angle x-ray scattering technique. This technique can be considered as an extension of the current OCD metrology technique. This Critical Dimension Small Angle X-Ray Scattering Technique (CD-SAXS) uses x-rays with wavelengths much smaller than circuit feature dimensions expected in many future IC generations. By illuminating a sample with a monochromatic x-ray beam and measuring its diffraction pattern(s) with a spatially resolved detector, the structure of the sample with its critical dimensions can be analyzed using well established techniques. This technique is also well suited to determine 3D structures consisting of the same materials as well as complex material structures such as the diffusion barrier coated on dielectrics used in the copper damascene process, a capability analogous to the x-ray crystallography technique that has achieved great success in understanding complex protein structures by examining their diffraction patterns.

Using the synchrotron radiation source at Argonne National Laboratory, Wu, et. al. have provided a first demonstration of the effectiveness of the CD-SAXS system to measure critical dimensions such as pitch, width, and height. They compared CD-SAXS measurement with CD-SEM using programmed LWR structures having trapezoidal profiles.

In summary, the pioneering works by Dr. Wenli Wu, et. al. shows that the CD-SXAS offers the following advantages. First, the x-ray wavelength is significantly shorter than the circuit feature size making the technique suitable for many future IC manufacturing generations providing good diffraction patterns and sensitivity. Second, simple data analysis is adequate to reconstruct the device structure (2D and 3D) because of the lack of multiple scattering. Third, the mass is measured instead of just geometry allowing a determination of line height roughness. Until now, the main drawback noted by Wu, et. al. is that the measurements using a laboratory x-ray source requires several hours per site. While that those time frames make the technique useful as a research and development tool, significant throughput improvement is required to make the CD-SAXS practical to meet the grand challenges for in-line IC metrology applications.

SUMMARY OF THE INVENTION

X-ray scatterometry provides high measurement accuracy and sensitivity due to its short wavelength, non-destructive capability due to potentially low dosages, and true 3D profile measurement because of its long penetration depth. It is ideally suited for existing CD metrology requirements and has ample potential for future needs.

The disclosed critical dimension grazing incidence small angle x-ray scatterometer system (CD-GISAXS) has the capability to address the three grand challenges, namely, Critical Dimension (CD) and $L_{eff}$ control in lithography, 3D metrology of etched gates (front end processes), and 3D structure characterization of resist profile (interconnects).

The disclosed CD-GISAXS achieves reduced measurement times by increasing throughput using the following technical innovation: use of longer wavelengths (~12×, in some cases) and x-rays in a reflective geometry to increase both the collimation acceptance angle of the incident beams and the scattering signal strength, resulting in a substantial combined throughput gain. This wavelength selection and geometry can result in a dramatic reduction in measurement time. Furthermore, the capabilities of the CD-GISAXS can be extended to meet many of the metrology needs of future generations of semiconductor manufacturing and nanostructure characterization, for example.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Theoretical basis for longer wavelengths:
The three grand metrology challenges all require measuring critical dimensions in 3D of structures with a linear dimension 45 nanometers (nm) or smaller. The measurements are sometimes made within a small area, known as the wafer test pad that is usually located inside the so-called scribe-line along which the chips are separated. The area is typically less than 100 micrometers (μm) on a side but the side along the scribe-line direction can be longer if necessary. For in-line metrology applications, the structures within the test pad are typically repeated periodic structures.

The throughput of a CD-SAXS system is proportional to both the x-ray flux incident on the test pad and the scattering strength (fraction of the incident x-rays scattered) by the structure within the test pad. Therefore, to improve the throughput of CD-SAXS with the problem as defined above, one needs to improve and optimize both of those parameters.

The x-ray flux F incident on the test pad area A can be expressed as:

$$F = \eta B_C L^2 \Delta\Omega^2, \quad (1)$$

where $\eta$ is the efficiency of the x-ray optical system relaying the x-rays from the source to the sample, $B_C$ the spectral brilliance of the x-ray source, L is the linear dimension of the test pad (a square test pad is assumed with $A=L^2$) and $\Delta\Omega$ the angular collimation required to achieve a given measurement precision. Eq. (1) shows that F is proportional to $\Delta\Omega^2$, which is s basis for a key innovation in the CD-GISAXS system described here.

Figure 1:
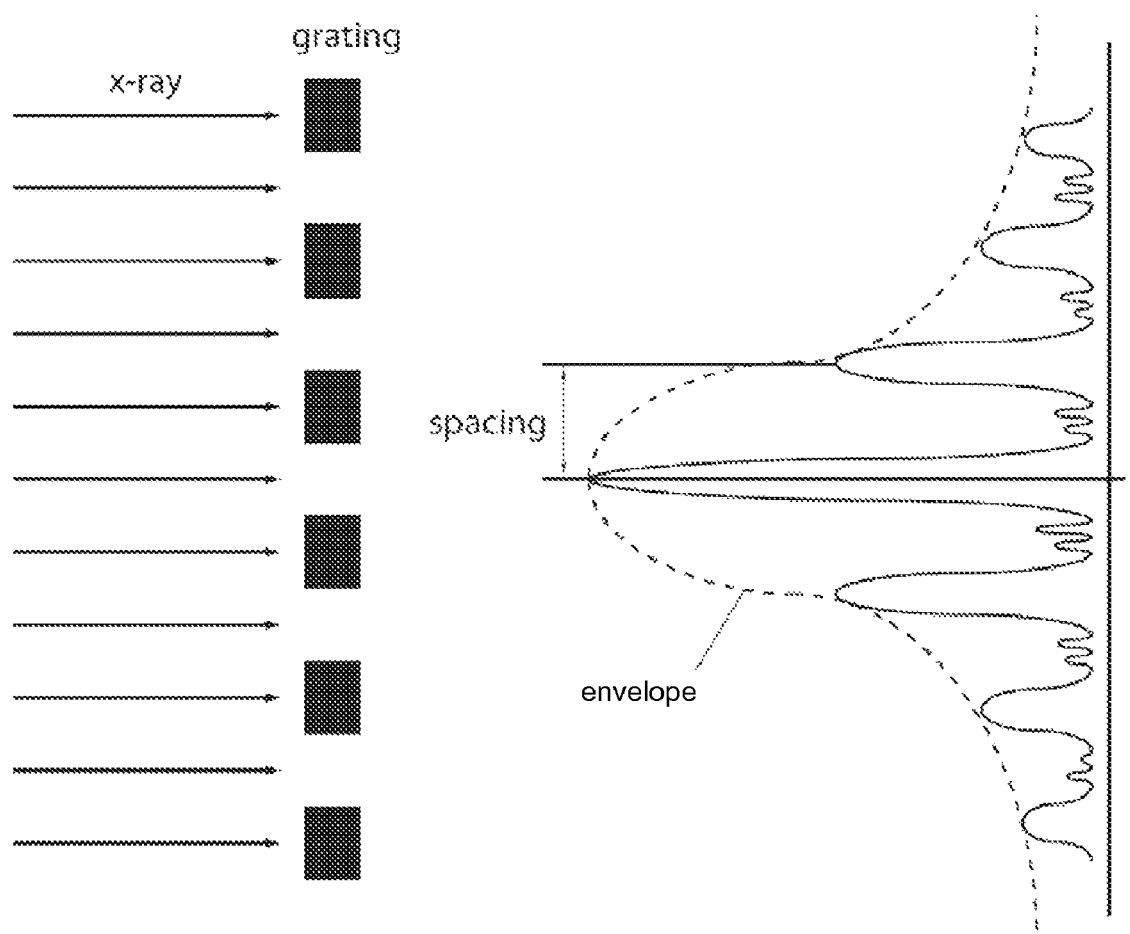
FIG. 1 is a schematic diagram illustrating the dependence of a diffraction pattern on a grating structure.

FIG. 1 shows the diffraction pattern resulting from a periodic grating: the spacing between the diffraction peaks is determined by the grating period while the overall envelope is determined by the width of the opening in each grating element. The angular positions of the peaks satisfy the grating equation:

$$2d \sin\theta = n\lambda,$$

where d is the repeat distance, $\theta$ is the diffraction angle, $\lambda$ is the wavelength, and n is the diffraction order. The grating equation shows that longer a wavelength leads to a larger diffraction angle. By differentiating the grating equation assuming that the wavelength of x-rays is fixed, one can further conclude that the collimation angle required, $\Delta\theta$, for achieving a given sampling between two diffraction peaks, is proportional to the x-ray wavelength. Therefore, longer wavelength x-rays are preferred for higher scattering throughput assuming other parameters in Eq. (1) are equal.

The above conclusion can be illustrated by considering a periodic structure with a 45 nm period. Using 17.4 keV x-rays with wavelength of 0.071 nm as used in the experiment by Wu, et al., the diffraction angle is $\theta = \lambda/2d = 0.071/90 = 0.79$ mrad. To sample this periodicity with an accuracy of 1%, the beam convergence angle must be confined to less than 7.9 μrad. In contrast, using a longer wavelength such as 1.49 keV x-rays (Al Kα line), the diffraction angular increases by a factor of 11.6 to 9.2 grad. At the same 1% sampling accuracy, the collimation angle can also be increased by a factor of 11.6 to 92 μrad. With samples in which features have comparable feature size in the sample plane across both x and y directions, this factor of 11.6 gain in the divergence angle leads to a solid angle gain of $11.6^2 \approx 136$. Because a larger proportion of the x-ray emitted from the source can be used for data acquisition, we obtain a x-ray flux gain by a factor of 136, a significant gain that will result in proportional throughput gain. Note that this gain in solid angle can be further increased by further decreasing the wavelength, for example, to EUV range. For example, using 13.4 nm EUV radiation, the diffraction angle and therefore the collimation angle increases by a factor of 189 and the illumination beam solid angle can be increased by a factor of 1892 or over 35,000.

In addition to the substantial gain in x-ray flux due to the use of longer wavelength x-rays, the longer wavelength also results in significant gain in the scattering signal strength for the small circuit structures to be measured. To quantify the scattering strength, consider the diffraction signal from a grating in the transmission geometry used by Wu, et. al. For a square wave profile grating with a unity line/space ratio, the diffraction pattern in general consists of a set of maxima corresponding to odd diffraction orders in addition to a non-diffracted (zero order diffraction) maximum. In order to achieve maximum diffraction efficiencies for the non-zero diffraction orders, the grating must be of sufficient thickness so that the phase shift experienced by the x-rays passing through the grating is equal to $\pi$ or its odd integer multiples. For a grating made of Si and Cu, the thickness required for producing $\pi$ relative phase shift is 1.6 µm, which is significantly larger than the height of circuit features to be measured. For a Si/Cu grating with 200 nm thickness, the diffraction efficiency for the first diffraction order is only 2.9% for 17.4 keV x-rays. However, this diffraction efficiency is increased to 23% when longer wavelength (1.5 keV) x-rays are used, an increase of about 8 times from that using 17.4 keV x-rays.

In summary, use of longer wavelength x-rays can significantly increase the throughput of a CD-SAXS system because it significantly increases both the acceptable angular collimation of the incident beam (resulting in an increased flux on the test pad) and the scattering signal strength. From a theoretical point of view, x-rays of wavelength longer than the wavelength examples provided would be preferred. In practice, suitable x-ray sources must be considered. In fact, using the selected x-ray wavelengths, the combined gain in throughput amounts to about 1,600 (multiplying the two numbers). This conclusion is used in the design the CD-GISAXS system.

Theoretical Basis for Grazing Incidence Geometry:

To maximize the advantage of long wavelength x-rays for improving throughput using a transmission geometry, it is required that the silicon (Si) substrate underneath the test pad be locally thinned since long wavelength x-rays have low transmission through the standard Si wafers in production today—the wafer thicknesses are typically about 750 µm. Although local thinning may be possible in the future, it is generally not preferred by IC manufacturers.

As a result, the preferred embodiment of the present invention is based on a Grazing Incidence Small Angle X-ray Scattering technique (GISAXS). GISAXS is a versatile technique for characterizing nano-scale structures at surfaces, under buried interfaces, or in thin films. It combines two very well established techniques: the scattering at small angles with X-rays, which allows the derivation of structural information in the range 1-100 nm, and off-specular scattering, which allows derivation of statistical information at scales that are greater than the interatomic distances. The GISAXS intensity distribution corresponds to off specular reflectivity and the intensity distribution parallel to the surface plane corresponds to a line cut through the corresponding transmission SAXS pattern. In past, this technique was exploited to study lateral correlations, sizes and shapes of semiconductors dots, of metallic islands, and of the self organized dots superlattices.

Figure 2:
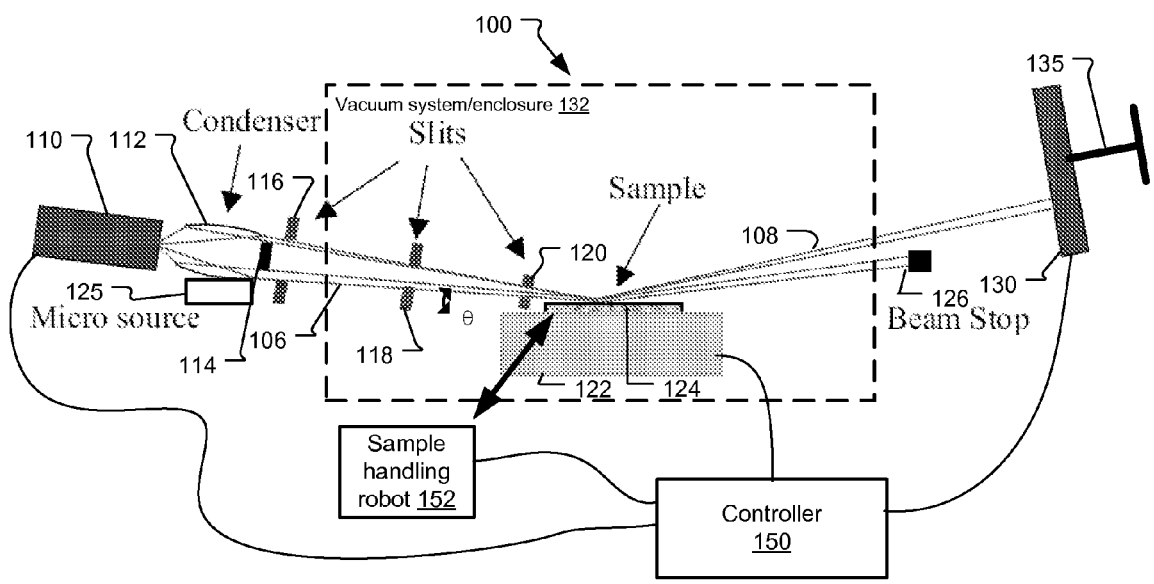
FIG. 2 is a schematic diagram of a CD-GISAXS system according to the present invention.

FIG. 2 shows a CD-GISAXS system 100, which has been constructed according to the principles of the present invention. This shows an additional practical advantage of the CD-GISAXS system 100: the reflective geometry makes measurements from the top side of the wafer sample 124.

A vacuum chamber 132 is preferably used to house at least some of the components of system 100 and should be constructed to be compatible with vacuum better than $10^{-7}$ Torr. The vacuum is useful to minimize absorption of the X-ray beam. As a result, some air gaps are usually used to ease maintenance and operation so that the source 110 and detector 130, for example, are not maintained in the vacuum.

In the preferred embodiment an electron bombardment x-ray source 110 is used to generate the X-rays. These devices have a cathode and an anode contained in a sealed vacuum tube. Thermal electrons generated at the cathode are accelerated towards the anode by the high voltage and bombard the target material at high energy to generate x-ray emission.

The emission spectrum of the electron bombardment x-ray source 110 contains sharp emission lines that are characteristic fluorescence emissions of the target element superimposed on a broad continuous Bremsstrahlung background radiation spectrum.

In one implementation, a micro-focus x-ray source is used. These sources contain simple electron-focusing devices that focus the electron beam into a spot from several micrometers to tens of micrometers in size when reaching the target, thus leading to a fine emission spot size with concentrated electron flux. In one example, the spot size is between 1 and 5 micrometers in diameter, although it can range between 0.1 and 30 micrometers.

In one embodiment, a structured anode target and high overvoltage source are used as described in U.S. patent application Ser. No. 11/609,266, filed Dec. 11, 2006, by Wenbing Yun et al., entitled Structured Anode X-ray Source for X-ray Microscopy, which application is incorporated herein in its entirely by this reference.

In another implementation, a rotating-anode source is used. This class of X-ray sources uses a spinning x-ray target to distribute the thermal load over the circumference of the anode. Rotating at rates of 6,000 to 12,000 revolutions per minute (rpm), these instruments can increase the spectral brilliance by over an order of magnitude to $10^9$-$10^{10}$ photons/ (mm$^2$ mrad$^2$ sec.), but with the drawbacks of increased complexity, mechanical vibration, and more maintenance requirements.

In the current embodiment, the source generates X-rays with wavelengths between 0.20 and 1 nm from an electron-bombardment source.

In other embodiment, ever longer wavelength radiation sources are used such sources of soft x-ray radiation with wavelengths between 1 and 10 nm and EUV radiation with wavelengths between 10 and 15 nanometers (nm). Such sources include laser-plasma source, gas-discharge sources, electron-bombardments sources, and synchrotron radiation sources.

A condenser 114 is used collect the X-rays from the source and concentrate them on the sample 124. A reflective lens configuration is currently preferred, with acceptance angle of 1 to 500 mrad. It preferably has inner surface with an elliptical shape where the source and sample surface are located at the foci or a parabolic shape, or a 2-reflection Wolter mirror shape.

In the preferred embodiment, the condenser 114 is a Wolter mirror condenser lens. This Wolter mirror is slightly focusing preferably having slope errors less than 80 grad optimized for this CD-GISAXS system 100. It is fabricated from hollow boro-silicate capillaries and the final condenser 114 will be have a length between 10 to 100 millimeters (mm) and a diameter of between 50 µm and 5 mm. Alternatively other x-ray focusing technologies can be used. Fresnel zone plate lenses, for example, provide the highest focusing resolution of up to tens of nanometers and efficiency of up to 20%.

The reflective lens is preferably constructed from a bulk material such as glass or metal such tungsten, gold or silver and a ceramic including $Al_2O_3$, tungsten carbide, or silicon carbide. A heavy metal surface coating of tungsten, gold or silver is also useful. However, in other examples, a glass capillary condenser is used with a reflective multilayer coating of, for example, heavy metal such as tungsten and gold. The use of such heavy elements increases the maximum reflection angle roughly in proportion to the atomic weight. This additional process may be used to increase the collimation angle achievable by the reflective condenser lens.

A central stop 114 functions as an energy filter to attenuate the undesirable Bremsstrahlung radiation and any emission from an undesirable emission lines to monochromatize the x-ray beam 106 to the desired emission line from the source 110. In one embodiment, the central stop 114 is a circular metal stop that is affixed to a membrane extending across the exit aperture of the condenser 114.

A series of collimating slits 116, 118, 120, function as energy filters to further collimate the x-ray beam to produce a well defined beam profile with small amounts of x-rays scattered outside this beam profile. In one implementation, a two slit system is implemented to shape the incident beam 106 and maximize the throughput of the system 100. A 3-slit configuration is used if the background scattering is too large.

A multi-axis sample positioning stage 122, such as a goniometer, is used to hold the sample 124 and position it within the beam 106. The position and orientation of the sample 124 with respect to the incident beam 106 are critical for proper interpretation of data. The stage 122 is preferably a high resolution horizontal 4-circle goniometer with x-axis, y-axis, and z-axis stages and a ω-2θ goniometer and an open Eulerian cradle to provide two additional axes of rotation ($-90°<\psi<90°$ and $-180°<\phi<180°$, where $\phi$ is the polar angle within the sample plane and $\psi$ is the azimuthal (or pitch) angle perpendicular from the sample plane, both measured from the incident x-ray beam's projection on the plane). The travel ranges of the XYZ stages are at least 25 millimeters (mm) and preferably 300 mm or more so that the system is capable of positioning to any point of a 12 inch wafer into the beam 106.

In one implementation, the x-ray source 110, focusing condenser 112, and the slits 116, 118, 120 are mounted on the fixed arm of the goniometer stage 122 and the detector 130 with the beam stop 126 are mounted on the 2θ arm.

A beam-stop 126 is positioned to remove the direct reflection of the beam 106 on the sample 124. A spatially-resolved detector system 130 detects the diffraction pattern in beam 108 from the sample.

For high-throughput data acquisition, a true photon counting detector with high counting rates, large dynamic range, and a small pixel size is preferred to achieve the best sensitivity and angular resolution. Thus, in one embodiment, a large format back-illuminated direct-detection CCD camera is used as the detector system 130. The camera preferably has a resolution of greater than 1000×1000 pixels, with 2048× 2048 pixels or more being preferred formats and 13.5 µm pixel size. The full-well capacity is 40,000 electrons or more. Each 1.5 keV x-ray photon absorption event will generate 500 electrons, given a dynamic range of 800, in excess of 9-bit equivalent. In comparison, the dark counts are on the order of several electrons.

The detector is also a two dimensional detector in the preferred embodiment. The recording of diffraction patterns in two orthogonal planes is important for 3D structure characterization including 3D structures consisting of similar materials or dissimilar materials such as diffusion barrier coated on an etched resist structure.

If required by the wavelength, a detector that is a scintillator-coupled CCD camera in which the scintillator coupling is made with an optical fiber taper or a lens is appropriate.

Alternative detector technologies including amorphous silicon detectors with or without multi-element photo-multiplier tubes are used in other implementations.

Multi-wire proportional counters (MWPC) and micro strip detectors are still other examples.

The following table 1 provides some detail concerning the configuration of the system 100 in one implementation.

TABLE 1

Design Parameters of CD-GISAXS

| Item | Specification |
| --- | --- |
| Source to Sample distance (mm): | 250-500 |
| Sample to Detector Distance (mm): | ~500 |
| Number of Slits | 2 |
| Angular Range in Diffuse Scattering Plane (deg) | 0-15 |
| Angular Range in Small Angle Scattering Plane (deg) | ±7.5 |
| $Q_{Min}$ (/nm) | 0.06 |
| Active Area of the CCD Detector (mm × mm) | 140 × 140 |
| Vacuum Requirement (Torr) | $10^{-7}$ |

The system controller 150 controls the operation of the system 100 including the source 110, sample stage 122, and detector 130. The controller 150 makes statistical measurements on pitch, linear size, height, side-wall taper angle, gate structure geometry, and/or interconnect structures of fabricated periodic structures of the sample 124 in response to the diffraction patterns, and preferably the two dimensional diffraction patterns, detected by the detector 130. This process is essentially the inverse of the forward modeling process. The analysis is preferably carried out using a combination of pattern matching and analytical algorithms.

The controller 150 further provides a graphical-user interface providing access to the modeling and structure determination algorithms. In one example, a user programs a set of measurement points on a wafer via the interface, with the option to load in the design data. The control system 150 then automatically loads the wafer sample 124 by control of the sample handling robot 152, positions the measurement regions into the scatterometer's beam 106 by operation of the sample stage 124 and acquires the diffraction data.

In the preferred embodiment, the controller 150 adjusts the sample stage 122 in response to the detector 130 to execute an initial alignment. Generally, focusing is considered unnecessary because of the long depth of field of the condenser optics 112. The angle settings of the stage 122 are adjusted iteratively until a symmetric diffraction pattern around the central beam stop is obtained. After this alignment step, diffraction patterns are acquired by the controller and the critical dimension measurements computed. The critical dimensions are computed by the controller 150 with the modeling algorithms and displayed to the operator along with a fail/pass signal based on whether the measured dimensions meets the margin specified by the design.

Wavelength Selection and Angle of Incidence:

The surface features reflect different amounts of incident light or x-rays, and the reflected light interferes to produce a diffraction pattern analogous to that of the transmission grating illustrated in FIG. 1. In the system 100, the small-angle x-ray scattering diffraction pattern is measured first, then it is used to determine the sample's critical dimensions using surface x-ray scattering theories developed in recent years, including data analysis algorithms for IC metrology applications.

An important consequence of using GISAXS is that the foot print of the incident beam 106 is scaled by 1/(sin θ) within the scattering plane, where θ is the grazing incidence angle. For a given foot print size like the finite size of the test pad, this beam spread means that the usable beam cross section within the scattering plane is only sin θ×L where L is the length of the test pad, limited typically to 100 μm and expandable if critically necessary. This constraint directly reduces the usable x-ray flux and must be considered in the overall throughput calculation. As will be shown below, longer wavelength x-rays are also advantageous as the required grazing incidence angle is roughly proportional to the x-ray wavelength. Therefore, longer wavelength x-rays are again preferred for achieving higher throughput.

Figure 3A:
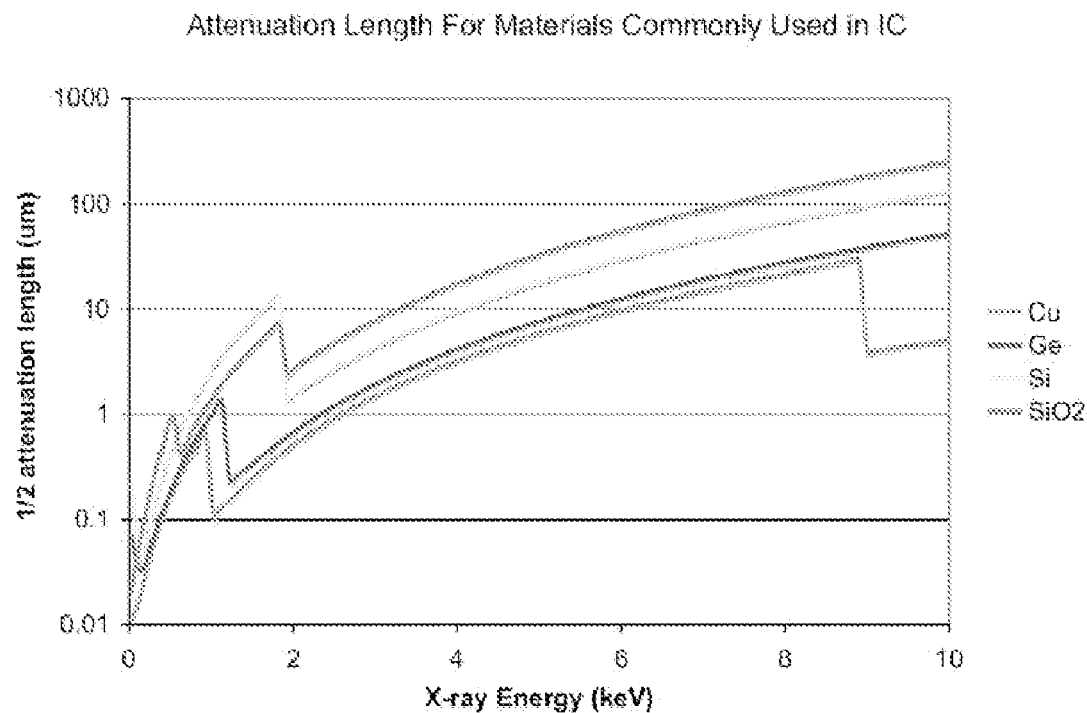
FIG. 3A is a plot of attenuation length in micrometers as a function of X-ray energy in kilo-electron-Volts (keV) for copper, germanium, silicon, and silicon dioxide.
Figure 3B:
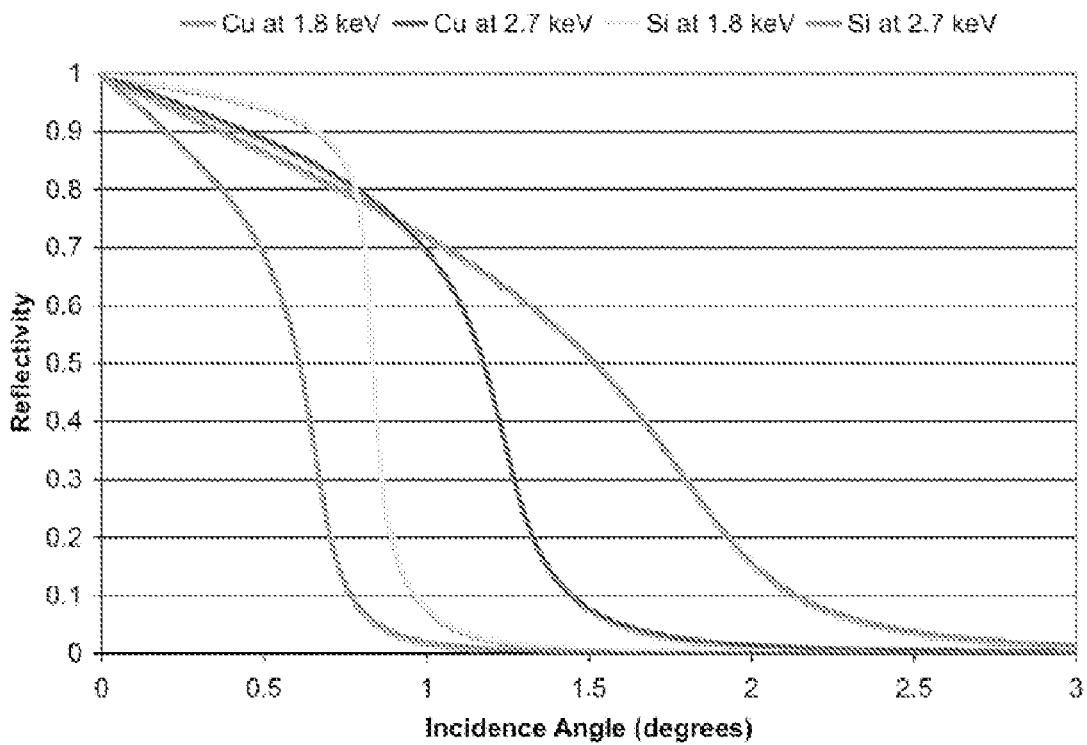
FIG. 3B is a plot of reflectivity as a function of incident angle for copper and silicon to radiation of 1.8 keV and 2.7 keV.

For a given metrology application, the grazing incidence angle θ needs to be carefully considered for achieving adequate probing depth and throughput. The depth of the interaction will depend on the x-ray energy and sample material composition. Lower energy and higher-Z material generally leads to shallower penetration depth, except at certain absorption edges. The 1/e attenuation length for photoresist, Cu, Si, $SiO_2$ and Ge as a function of x-ray energy is shown in FIG. 3A and reflectivity of PMMA, Si and Cu are shown in FIG. 3B as a function of grazing angle for 1.5 keV Kα emission from aluminum. Features fabricated on an IC have a thickness of about 200 nm at lower layers with finer features and up to several micrometers for upper levels with more coarse features. Based on the data shown in FIGS. 3A and 3B, 1.5 keV x-ray radiation is sufficient for probing several levels of lower layer features. A grazing incidence angle of 1.05 degree (line A marked in FIG. 3B) provides excellent contrast between Si and photoresist and this angle can be used to examine gate structures in front-end of the line processes. At this incidence angle, the beam is smeared by a factor of 1/sin(1.05)≈54.6 in the scattering plane, leading to a corresponding reduction in incidence x-ray flux at the test pad. Furthermore, a 1.38 degree incidence angle (line B marked in FIG. 3B) provides the best contrast between Si and Cu, and therefore is well suited for examining Cu lines in back-end of the line metrology applications. This larger angle leads to a flux reduction factor of 41.5 from the smearing.

Source Wavelength Selection

Currently, based on extensive numerical simulations and taking into consideration suitable x-ray sources, results suggest 1.5 keV x-rays from an Al target is the optimal choice for building a practical CD-GISAXS tool.

Longer wavelength radiation leads to larger diffraction angles and greater scattering cross-sections, however. As a result, in other embodiment even longer wavelengths are used such as wavelengths of between 1 and 15 nanometers.

The longer wavelengths are preferred because each factor depends on the square of the wavelength and they combine to produce an overall throughput dependence of $\lambda^4$ or $E^{-4}$. With in-air applications, the wavelength selection is generally limited by x-ray attenuation, but much wider range of wavelength can be used with in-vacuum instruments, for example soft x-ray with several nanometers wavelength and extreme ultraviolet (EUV) radiation with wavelength of around 10 nm are possible. Deep UV (DUV) radiation with tens of nanometers wavelength can also be used, but it has a limitation that its wavelength scale approaches the features to be examined. Compared with the 1.49 keV x-ray from Al K-α line described previously, soft x-ray at 392 eV (λ=3.16 nm from Nitrogen K-α line) gives a throughput gain of over 200 and EUV radiation at 103 eV (λ=13.4 nm) gives a throughput gain of over 40,000.

The use of the long wavelength radiation also allows the use of additional x-ray source generation technologies instead of traditional electron bombardment sources, including laser-plasma, gas-discharge, and plasma-pinch sources that are able to generate even higher emission brilliance. For example, laser-plasma sources have been demonstrated to be able to generate x-rays with energy up to 392 eV and a number of high-performance systems operating at EUV wavelengths have been developed for next generation lithography application. These system are capable of generating brilliance of $10^{11}$-$10^{13}$ photons/($mm^2$ $mrad^2$ sec), which is about 10-1,000 times higher than the performance limit of conventional electron-bombardment x-ray sources. This factor, combined with the factor from the longer wavelength, a metrology system with these high-performance sources operating at these longer wavelengths is able to acquire data with sub-second exposure time and provide high-throughput capability for the semiconductor metrology applications.

Numerical Simulation of the CD-GISAXS for IC Metrology Applications:

Reflected x-ray radiation will be recorded with the preferably large-format CCD camera 130. With periodic line structures such as IC interconnects oriented with the lines parallel to the CCD array of the camera detector 130, the diffraction image is a similar pattern to a grating diffraction. The peak-to-peak distance in the diffraction pattern is related to the interconnect line spacing; the peak envelope is determined by the width of interconnects. The diffraction pattern is also sensitive to feature height, line height roughness (LHR), and side wall profile.

For a finite periodic array, the width of the diffraction peaks widens and the pattern overall is a rich source of information from which the nature of the structure can be inferred. The scattering amplitude may be estimated using the formalism developed for diffraction gratings: using $\psi=\pi-\alpha_i$ and $\phi=\pi-\alpha_j$, the grating equation can be written as $$m\lambda = d(\sin\psi + \sin\phi),$$

where m is the diffraction order and d is the grating spacing. The diffraction theory for arbitrary line profiles has been developed by Naviere and Petit provided that there is no variation along the grooves. In the simplest case, that of a laminar grating with rectangular profiles of groove depth h, period d, and equal land and groove widths. The heights of the peaks are predicted to be:

$$E_0 = \frac{R}{4}\left[1 + 2(1-P)\cos\left(\frac{4\pi h \cos\psi}{\lambda}\right) + (1-P)^2\right]$$

$$E_m = \begin{cases} \frac{R}{m^2\pi^2}[1 - 2\cos Q^+ \cos(Q^- + \delta) + \cos^2 Q^+] & m = \text{odd} \\ \frac{R}{m^2\pi^2}\cos^2 Q^+ & m = \text{even} \end{cases}$$

where $$P = \frac{4h\tan\psi}{d}, \quad Q^\pm = \frac{m\pi h}{d}(\tan\psi \pm \tan\varphi), \quad \delta = \frac{2\pi h}{\lambda}(\cos\psi + \cos\varphi),$$

and $$R = \sqrt{\psi\varphi}.$$

Note that while the position of the peaks depends only on the period d, the peak heights depend in a sensitive way on the groove depth h.

Figure 4A:
FIGS. 4A and 4B illustrate CD's for an exemplary structure.
Figure 4B:
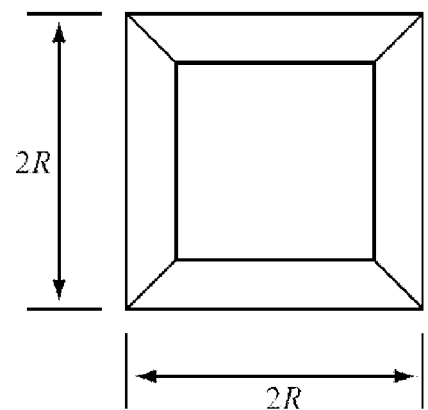

The diffraction patterns were simulated using IsGISAXS (R. Lazzari, J. Appl. Cryst. "*IsGISAXS: a program for grazing-incidence small-angle X-ray scattering analysis from* supported islands", 35, 406-421 (2002); the software "IsGISAXS" can be downloaded from the website http://www.esrf.fr/computing/scientic/joint projects/IsGISAXS/) within the framework of Distorted Wave Born Approximation for a series of infinitely repeating square patterns with sloping side walls shown in FIGS. 4A and 4B. To better reproduce the real data, we have accounted for the size-position coupling and used the Local Monodisperse Approximation.

The following sets of figures show the influences on the diffraction pattern from small changes in the feature size, height, periodic spacing pitch, and incidence angle. The simulations were made with the beam axis parallel to the square array pattern, so the diffraction has mirror symmetry and only one half of the diffraction pattern is shown.

Figure 5A:
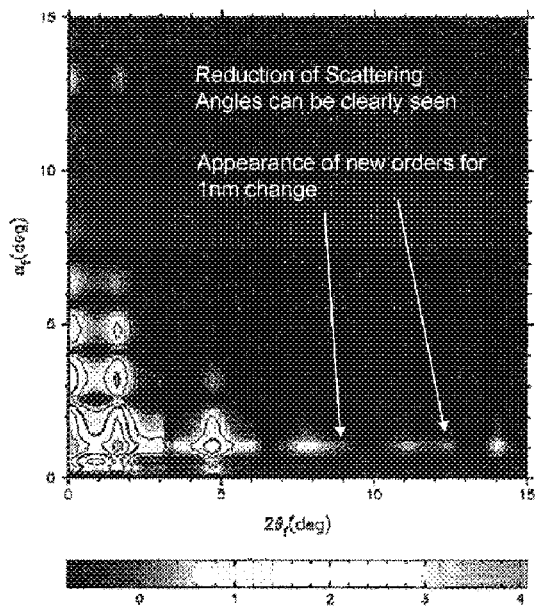
FIGS. 5A-5D show simulated diffraction patterns from a small change in: A periodic pitch spacing from 1 nanometer (nm) to B 3 nm; C feature width from 0.1 nm to D at 1 nm.
Figure 5B:
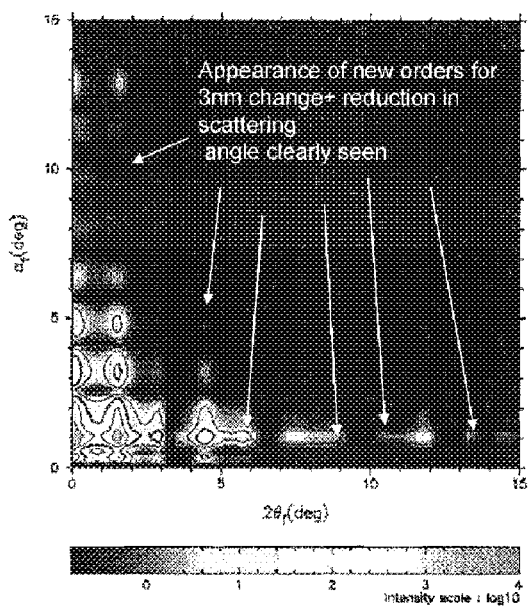

FIGS. 5A and 5B show how the diffraction pattern changes from a 1 nm and 3 nm change in pitch from 30 nm to 31 nm and 33 nm for perfect square columns, respectively. The simulation uses 1.5 keV x-ray radiation. A shift in the peak position is observed.

Figure 5C:
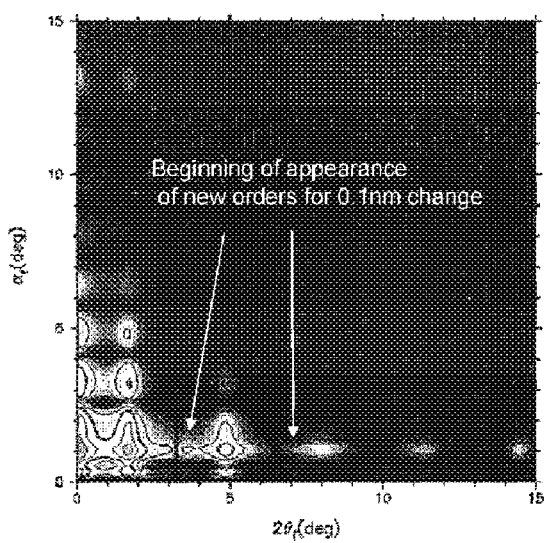
Figure 5D:
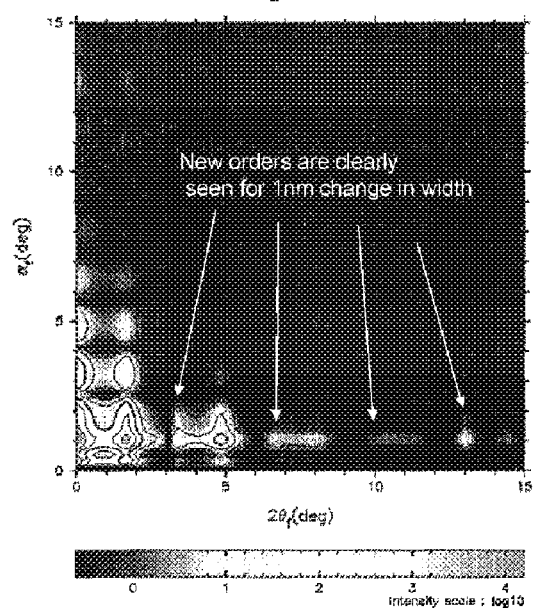

FIGS. 5C and 5D show the diffraction pattern changes from a 0.1 nm and 1 nm change in the column width from 15 nm to 15.1 nm and 16 nm respectively. For a 0.1 nm change in width, new orders begin to appear which are clearly seen for a 1 nm change in width.

Figure 6A:
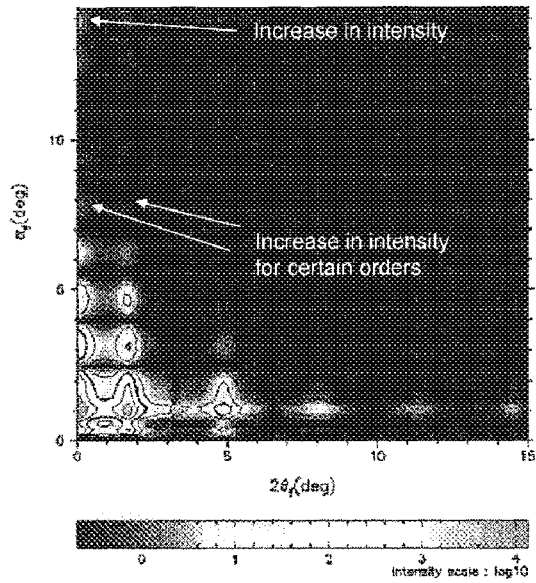
FIGS. 6A-6D show simulated diffraction patterns from a small change in A height from 1 nm to B at 3 nm; C base angle from 1 degree to D at 5 degrees.
Figure 6B:
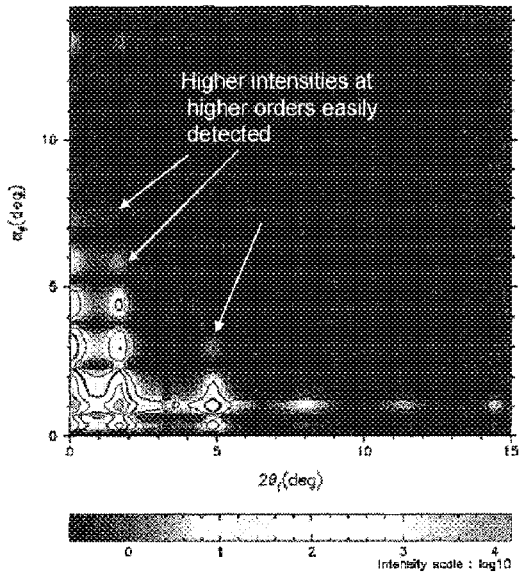
Figure 6C:
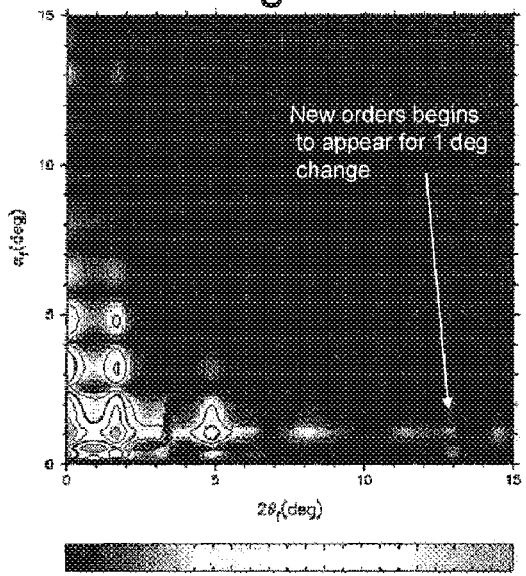
Figure 6D:
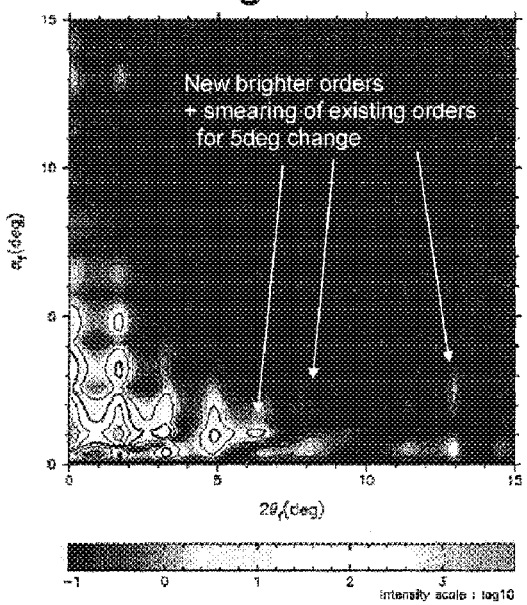

FIGS. 6A and 6B show the diffraction pattern changes resulting from a 1 nm and 3 nm change in the column height from 30 nm to 31 nm and 33 nm. The diffraction pattern shows clear change in the peak height. FIGS. 6C and 6D show the diffraction pattern changes resulting from a 1 degree and 5 degree change in the base angle from 90 degrees to 89 degrees and 85 degrees. Substantial smearing of peaks can be noticed when the angle changes by 5 degrees. These changes provide sufficient signal to measure quantitatively and characterize the sample in a critical dimension metrology measurement. Furthermore, this technique can also be used as an extremely sensitive tool to compare samples fabricated under different processing parameters or from different batches of production.

These simulations demonstrate the ability of CD-GISAXS to characterize nearly all aspects of a periodic surface and surface features. In addition to use of a laboratory x-ray source, this technique can also be used with synchrotron radiation sources, which provide an additional powerful advantage of continuously tunable energy and high degree of collimation. These two additional features can be used to gain elemental sensitivity, for example, to study the tantalum encapsulation layers in the Damascene process.

Source Beam Requirements

The square test pad structure preferred by IC manufacturers requires that the illumination beam 106 in the CD-GISAXS 100 has a rectangular cross section with one side significantly larger than the other side (see FIG. 2). For a square test pad 100 μm on a side, the beam cross section in the scattering plane is approximately equal to 100 sin θμm while the cross section normal to the scattering plane is 100 μm. For $\theta=1$ degree, $\sin\theta \approx 0.017$ and thus the beam cross section in the scattering plane is 1.7 μm. The dimension of the test pad along the scribe-line direction can be extended to up to 1 mm if necessary. In this case, the beam cross section in the scattering plane can be increased by a factor of 10, making the beam cross section less asymmetric and increasing the measurement throughput accordingly. Here, the throughput estimated is based on a square test pad, not the more favorable rectangular pad.

To obtain a rectangular beam profile, a line x-ray source with the long direction of the line arranged to be normal to the scattering plane is preferred. A reasonable source dimension for 1.5 keV x-ray from Al is $1\times 10\,\mu m^2$. The exact source size configuration will depend on the radiation energy as incidence angle changes with the energy. In one configuration, the Wolter mirror condenser lens 112 is used to collect the x-rays generated from the x-ray source 110 and produce a magnified image, preferably between 5 and 15 times, or about 10 times magnification, on the surface of a wafer 124 on which measurement is to be made. The foot print of this beam is 100 μm by $10/\sin\theta \approx 573$ μm for $\theta=1$ degree, with the latter being in the scattering plane. To reduce the foot print of the beam in the scattering plane to 100 μm to match the dimension of the standard test pad, the three slits 116, 118, 120 are used.

In the preferred embodiment of the system 100, the Wolter mirror lens 112 is mounted on a multi-axis stage 125 to provide linear focusing motion and 2-rotation axes to control the incidence angle. The detector camera 130 preferably has a detector stage system 135 that has 2 rotation, yaw and pitch motion stages 135 and a translational motion stage to control its distance to the sample 124.

While this invention has been particularly shown and described with references to preferred embodiments thereof, it will be understood by those skilled in the art that various changes in form and details may be made therein without departing from the scope of the invention encompassed by the appended claims.

What is claimed is:

1. A critical dimension X-ray scatterometry system, comprising:
a laboratory radiation source for generating extreme ultraviolet (EUV) or X-ray radiation with an energy of 1.5 KeV or less;
an x-ray focusing optic for projecting the radiation as a beam towards a sample;
a sample stage for holding the sample in reflective geometry; and
a two-dimensional spatially resolved detector, comprising a two-dimensional array of pixels, for measuring diffraction patterns generated by the interaction of the beam with the sample.

2. A system as claimed in claim 1, further comprising a beam stop for blocking specular reflection of the beam from the sample.

3. A system as claimed in claim 1, wherein the radiation is EUV radiation with a wavelength between 10 and 15 nanometers (nm).

4. A system as claimed in claim 1, wherein the radiation is soft x-ray radiation with wavelength between 1 and 10 nm.

5. A system as claimed in claim 1, wherein the radiation is x-ray radiation with wavelength between 0.83 and 1 nm.

6. A system as claimed in claim 1, wherein the radiation source is a laser-plasma source.

7. A system as claimed in claim 1, wherein the radiation source is a gas-discharge source.

8. A system as claimed in claim 1, wherein the radiation source is an electron-bombardment source.

9. A system as claimed in claim 1, wherein the radiation source is a rotating-anode x-ray source.

10. A system as claimed in claim 1, wherein the radiation source is a micro-focused x-ray source with spot size between 0.1 and 30 micrometers.

11. A system as claimed in claim 1, wherein the radiation source generates a radiation with an asymmetric shape that is elongated in the direction perpendicular to the sample compared with the parallel direction.

12. A system as claimed in claim 1, wherein the x-ray focusing optic is a reflective lens.

13. A system as claimed in claim 1, wherein the x-ray focusing optic has an elliptical shape where the source and sample surface are located at the foci.

14. A system as claimed in claim 1, wherein the x-ray focusing optic has a parabolic shape.

15. A system as claimed in claim 1, wherein the x-ray focusing optic is a Wolter mirror type containing two suitable reflecting surfaces.

16. A system as claimed in claim 1, wherein the x-ray focusing optic comprises bulk material comprised of glass, metal including tungsten gold or silver, or a ceramic including Al2O3, tungsten carbide, or silicon carbide.

17. A system as claimed in claim 1, wherein the x-ray focusing optic comprises a heavy metal coating of tungsten, gold or silver on reflecting surfaces.

18. A system as claimed in claim 1, wherein the x-ray focusing optic comprises a glass bulk material with a reflective multilayers coating of silicon and molybdenum.

19. A system as claimed in claim 1, wherein the x-ray focusing optic is a Fresnel zone plate lens.

20. A system as claimed in claim 1, wherein the x-ray focusing optic has an acceptance angle of 1 to 500 mrad.

21. A system as claimed in claim 1, wherein the detector comprises a direct-detection type camera with a back-illuminated chip.

22. A system as claimed in claim 1, wherein the detector comprises a scintillator-coupled CCD camera.

23. A system as claimed in claim 22, wherein scintillator coupling is made with an optical fiber taper.

24. A system as claimed in claim 22, wherein scintillator coupling is made with a lens.

25. A system as claimed in claim 1, wherein the detector comprises an amorphous silicon detector.

26. A system as claimed in claim 1, wherein the detector comprises a multi-element photo-multiplier tube.

27. A system as claimed in claim 1, wherein the sample is an integrated circuit wafer in a production line.

28. A system as claimed in claim 1, wherein the sample comprises an array of repeating man-made nanostructures.

29. A system as claimed in claim 1, further comprising a controller that makes statistical measurements on a pitch of fabricated periodic structures of the sample in response to the two-dimensional diffraction patterns that are detected by the detector.

30. A system as claimed in claim 1, further comprising a controller that makes statistical measurements on a linear size of fabricated periodic structures of the sample in response to the two-dimensional diffraction patterns that are detected by the detector.

31. A system as claimed in claim 1, further comprising a controller that makes statistical measurements on a height of fabricated periodic structures of the sample in response to the two-dimensional diffraction patterns that are detected by the detector.

32. A system as claimed in claim 1, further comprising a controller that makes statistical measurements on side-wall taper angle of fabricated periodic structures of the sample in response to the two-dimensional diffraction patterns that are detected by the detector.

33. A system as claimed in claim 1, further comprising a controller that makes statistical measurements on gate structure geometry of fabricated periodic structures of the sample in response to the two-dimensional diffraction patterns that are by the detector.

34. A system as claimed in claim 1, further comprising a controller that makes statistical measurements on interconnect structures of the sample in response to the two-dimensional diffraction patterns that are detected by the detector.

35. A system as claimed in claim 1, wherein the two-dimensional spatially resolved detector has a resolution of greater than 1000×1000 pixels.

36. A critical dimension X-ray scatterometry analysis method, comprising:
   generating extreme ultraviolet (EUV) or X-ray radiation with an energy of 1.5 KeV or less;
   projecting the radiation as a beam towards a sample;
   holding the sample in reflective geometry in the beam; and
   measuring diffraction patterns, with a two-dimensional spatially resolved detector comprising a two-dimensional array of pixels, that are generated by the interaction of the beam with the sample.

37. A method as claimed in claim 36, further comprising blocking specular reflection of the beam from the sample.

38. A method as claimed in claim 36, wherein the radiation is EUV radiation with a wavelength between 10 and 15 nanometers (nm).

39. A method as claimed in claim 36, wherein the radiation is soft x-ray radiation with wavelength between 1 and 10 nm.

40. A method as claimed in claim 36, wherein the radiation is x-ray radiation with wavelength between 0.83 and 1 nm.

41. A method as claimed in claim 36, wherein the step of projecting the radiation comprises reflecting the radiation with a reflective lens.

42. A method as claimed in claim 36, wherein the step of projecting the radiation comprises focusing the radiation with a Fresnel zone plate lens.

43. A method as claimed in claim 36, further comprising removing the sample from an integrated circuit wafer production line.

44. A method as claimed in claim 36, further comprising making statistical measurements on a pitch of fabricated periodic structures of the sample in response to the diffraction patterns.

45. A method as claimed in claim 36, further comprising making statistical measurements on a linear size of fabricated periodic structures of the sample in response to the diffraction patterns.

46. A method as claimed in claim 36, further comprising making statistical measurements on a height of fabricated periodic structures of the sample in response to the diffraction patterns.

47. A method as claimed in claim 36, further comprising making statistical measurements on side-wall taper angle of fabricated periodic structures of the sample in response to the diffraction patterns.

48. A method as claimed in claim 36, further comprising making statistical measurements on gate structure geometry of fabricated periodic structures of the sample in response to the diffraction patterns.

49. A method as claimed in claim 36, further comprising making statistical measurements on interconnect structures of the sample in response to the diffraction patterns.

50. A method as claimed in claim 36, wherein the sample comprises an array of repeating man-made nanostructures.

51. A method as claimed in claim 36, wherein the two-dimensional spatially resolved detector has a resolution of greater than 1000×1000 pixels.

52. A critical dimension X-ray scatterometry system, comprising:
   a laboratory radiation source for generating extreme ultraviolet (EUV) or X-ray radiation with an energy less than 2.7 KeV;

an x-ray focusing optic for projecting the radiation as a beam towards a sample;
a sample stage for holding the sample in reflective geometry; and
a two-dimensional spatially resolved detector, comprising a two-dimensional array of pixels, for measuring diffraction patterns generated by the interaction of the beam with the sample.

53. A system as claimed in claim 52, further comprising a beam stop for blocking specular reflection of the beam from the sample.

54. A system as claimed in claim 52, wherein the radiation source is a rotating-anode x-ray source.

55. A system as claimed in claim 52, wherein the radiation source is a micro-focused x-ray source with spot size between 0.1 and 30 micrometers.

56. A system as claimed in claim 52, wherein the radiation source generates a radiation with an asymmetric shape that is elongated in the direction perpendicular to the sample compared with the parallel direction.

57. A system as claimed in claim 52, wherein the x-ray focusing optic is a reflective lens.

58. A system as claimed in claim 52, wherein the x-ray focusing optic is Wolter mirror type containing two suitable reflecting surfaces.

59. A system as claimed in claim 52, wherein the x-ray focusing optic is a Fresnel zone plate lens.

60. A system as claimed in claim 52, wherein the detector comprises a direct-detection type camera with a back-illuminated chip.

61. A system as claimed in claim 52, wherein the sample is an integrated circuit wafer in a production line.

62. A system as claimed in claim 52, further comprising a controller that makes statistical measurements on a pitch of fabricated periodic structures of the sample in response to the two dimensional diffraction patterns that are detected by the detector.

63. A system as claimed in claim 52, further comprising a controller that makes statistical measurements on a linear size of fabricated periodic structures of the sample in response to the two dimensional diffraction patterns that are detected by the detector.

64. A system as claimed in claim 52, further comprising a controller that makes statistical measurements on a height of fabricated periodic structures of the sample in response to the two dimensional diffraction patterns that are detected by the detector.

65. A system as claimed in claim 52, further comprising a controller that makes statistical measurements on side-wall taper angle of fabricated periodic structures of the sample in response to the two dimensional diffraction patterns that are detected by the detector.

66. A system as claimed in claim 52, further comprising a controller that makes statistical measurements on gate structure geometry of fabricated periodic structures of the sample in response to the two dimensional diffraction patterns that are detected by the detector.

67. A system as claimed in claim 52, further comprising a controller that makes statistical measurements on interconnect structures of the sample in response to the two dimensional diffraction patterns that are detected by the detector.

68. A system as claimed in claim 52, wherein the spatially resolved detector is spatially resolved in two orthogonal directions.

69. A system as claimed in claim 52, wherein the radiation is EUV radiation with a wavelength between 10 and 15 nanometers (nm).

70. A system as claimed in claim 52, wherein the radiation is soft x-ray radiation with wavelength between 1 and 10 nm.

71. A system as claimed in claim 52, wherein the two-dimensional spatially resolved detector has a resolution of greater than 1000×1000 pixels.

* * * * *